United States Patent
Oh et al.

(10) Patent No.: US 9,483,821 B2
(45) Date of Patent: Nov. 1, 2016

(54) METHOD AND ULTRASOUND APPARATUS FOR DISPLAYING ULTRASOUND IMAGE CORRESPONDING TO REGION OF INTEREST

(71) Applicant: SAMSUNG MEDISON CO., LTD., Hongcheon-gun, Gangwon-do (KR)

(72) Inventors: Dong-Hoon Oh, Gangwon-do (KR); Dong-Gyu Hyun, Gangwon-do (KR)

(73) Assignee: Samsung Medison Co., Ltd., Hongcheon-gun, Gangwon-do (KR)

(*) Notice: Subject to any disclaimer, the term of this patent is extended or adjusted under 35 U.S.C. 154(b) by 78 days.

(21) Appl. No.: 14/560,967

(22) Filed: Dec. 4, 2014

(65) Prior Publication Data

US 2015/0213597 A1    Jul. 30, 2015

(30) Foreign Application Priority Data

Jan. 28, 2014   (KR) .................. 10-2014-0010884

(51) Int. Cl.
| | |
|---|---|
| G06K 9/00 | (2006.01) |
| A61B 8/00 | (2006.01) |
| G06T 7/00 | (2006.01) |
| G01S 7/52 | (2006.01) |
| G06K 9/46 | (2006.01) |

(Continued)

(52) U.S. Cl.
CPC ............ G06T 7/0012 (2013.01); A61B 8/461 (2013.01); A61B 8/463 (2013.01); A61B 8/469 (2013.01); G01S 7/52063 (2013.01); G01S 7/52068 (2013.01); G06K 9/46 (2013.01); G06T 15/00 (2013.01); G01S 7/52074 (2013.01); G01S 15/8979 (2013.01); G06K 2009/4666 (2013.01)

(58) Field of Classification Search
USPC ........ 382/100, 103, 106–107, 128–134, 153, 382/162, 168, 172–173, 181, 193–196, 209, 382/219, 232, 254, 274, 276, 285–291, 382/312; 367/103; 600/438, 437; 128/916; 703/2
See application file for complete search history.

(56) References Cited

U.S. PATENT DOCUMENTS

| | | | | |
|---|---|---|---|---|
| 6,464,642 | B1 * | 10/2002 | Kawagishi | .............. A61B 8/14 128/916 |
| 7,678,048 | B1 * | 3/2010 | Urbano | .................... A61B 8/00 367/103 |
| 2006/0241458 | A1 | 10/2006 | Hayashi et al. | |

(Continued)

FOREIGN PATENT DOCUMENTS

| | | |
|---|---|---|
| EP | 0 770 352 A1 | 5/1997 |
| EP | 2705798 A1 | 3/2014 |

(Continued)

OTHER PUBLICATIONS

Extended European Search Report dated Jun. 29, 2015, issued in corresponding European Patent Application No. 14190615.6.

Primary Examiner — Seyed Azarian
(74) Attorney, Agent, or Firm — McDermott Will & Emery LLP

(57) ABSTRACT

Provided is an ultrasound image display method. The ultrasound image display method includes displaying an ultrasound image of an object, selecting at least one region of interest (ROI) in the ultrasound image based on a user input, converting image pixel information corresponding to the at least one ROI into height values, and three-dimensionally displaying a partial ultrasound image corresponding to the at least one ROI by using the height values.

30 Claims, 17 Drawing Sheets

(51) Int. Cl.
  *G06T 15/00* (2011.01)
  *G01S 15/89* (2006.01)

(56) References Cited

U.S. PATENT DOCUMENTS

2008/0051661 A1 2/2008 Kataguchi et al.
2013/0060540 A1* 3/2013 Frahm .................... G06T 15/06
 703/2
2013/0184578 A1* 7/2013 Lee .......................... A61B 8/06
 600/438

FOREIGN PATENT DOCUMENTS

| JP | H11327 A | 1/1999 | | |
|----|----------|--------|---|---|
| JP | 2006-350724 A | 12/2006 | | |
| JP | 2008-080106 A | 4/2008 | | |
| KR | EP2705798 A1 * | 1/1999 | ............... | A61B 8/08 |
| WO | 2007/058632 A1 | 5/2007 | | |
| WO | 2009/079769 A1 | 7/2009 | | |

\* cited by examiner

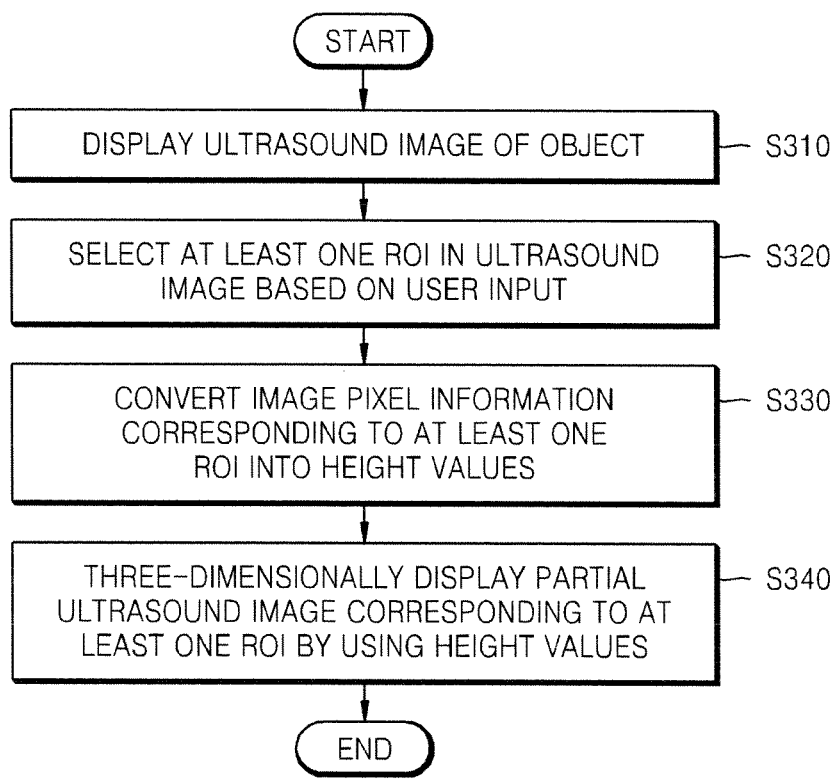

METHOD AND ULTRASOUND APPARATUS FOR DISPLAYING ULTRASOUND IMAGE CORRESPONDING TO REGION OF INTEREST

RELATED APPLICATION

This application claims the benefit of Korean Patent Application No. 10-2014-0010884, filed on Jan. 28, 2014, in the Korean Intellectual Property Office, the disclosure of which is incorporated herein in its entirety by reference.

BACKGROUND

1. Field

One or more exemplary embodiments relate to ultrasound image display methods and ultrasound apparatuses for displaying an ultrasound image corresponding to a region of interest (ROI) as a three-dimensional (3D) image having height values.

2. Description of the Related Art

An ultrasound diagnosis apparatus transfers an ultrasound signal from a body surface of an object to a predetermined region in a body of the object, and obtains a tomogram of a soft tissue or an image of a bloodstream by using information of an ultrasound signal reflected from a tissue in the body.

The ultrasound diagnosis apparatus is small and inexpensive and may display images in real time. Also, since the ultrasound diagnosis apparatus has high safety due to no exposure to X-rays or the like, the ultrasound diagnosis apparatus is widely used along with other image diagnosis apparatuses such as an X-ray diagnosis apparatus, a computerized tomography (CT) scanner, a magnetic resonance imaging (MRI) apparatus, and a nuclear medicine diagnosis apparatus.

Since values measured by the ultrasound diagnosis apparatus are closely related to a lesion diagnosis or the like, the accuracy of the values is required. Therefore, there is a need for a system that enables a user to accurately understand an ultrasound image.

SUMMARY

One or more exemplary embodiments include ultrasound image display methods and ultrasound apparatuses for displaying an ultrasound image corresponding to a region of interest (ROI) as a three-dimensional (3D) image having a height value.

Additional aspects will be set forth in part in the description which follows and, in part, will be apparent from the description, or may be learned by practice of the presented exemplary embodiments.

According to one or more exemplary embodiments, an ultrasound image display method includes: displaying an ultrasound image of an object; selecting at least one ROI in the ultrasound image based on a user input; converting image pixel information corresponding to the at least one ROI into height values; and three-dimensionally displaying a partial ultrasound image corresponding to the at least one ROI by using the height values.

The ultrasound image may include at least one of a brightness (B) mode image, a color Doppler image, a spectral Doppler image, a tissue Doppler image, an elasticity image, and a motion (M) mode image.

The image pixel information may include at least one of a brightness value, a speed value, a color value, an elasticity value, an amplitude value of a sound reflection signal, and a sound impedance value.

The selecting of the at least one ROI may include selecting an ROI of a predetermined size based on a point selected by a user.

The selecting of the at least one ROI may include selecting a region, which has a predetermined similarity value or more with respect to pattern information of a point selected by a user, in the ultrasound image as the ROI.

The converting of the image pixel information into the height values may include determining a sign of the height values based on movement direction information of a tissue or a bloodstream when the ultrasound image is a color Doppler image or a spectral Doppler image.

The three-dimensional displaying of the partial ultrasound image corresponding to the at least one ROI may include two-dimensionally displaying other images in the ultrasound image except the partial ultrasound image corresponding to the at least one ROI.

The three-dimensional displaying of the partial ultrasound image corresponding to the at least one ROI may include displaying the three-dimensional (3D) partial ultrasound image overlappingly on the ultrasound image which is a two-dimensional (2D) form.

The displaying of the 3D partial ultrasound image overlappingly on the ultrasound image which is the 2D form may include applying a semitransparent effect or a transparent effect to other images in the ultrasound image which is the 2D form except a region in which the 3D partial ultrasound image is overlappingly displayed.

The three-dimensional displaying of the partial ultrasound image corresponding to the at least one ROI may include three-dimensionally displaying the partial ultrasound image in a region different from a region in which the ultrasound image is displayed.

The ultrasound image display method may further include adjusting at least one of a position, a rotation angle, and a size of the three-dimensionally displayed partial ultrasound image.

The ultrasound image display method may further include displaying at least one of an average height value, a maximum height value, a minimum height value, and a variance value of the partial ultrasound image.

The three-dimensional displaying of the partial ultrasound image corresponding to the at least one ROI may include three-dimensionally displaying the partial ultrasound image by using a light source-based rendering method.

The three-dimensional displaying of the partial ultrasound image corresponding to the at least one ROI may include: receiving a selection of at least one rendering method among a plurality of rendering methods; and three-dimensionally displaying the partial ultrasound image by the selected rendering method.

The at least one ROI may include a plurality of ROIs, and the three-dimensional displaying of the partial ultrasound image corresponding to the at least one ROI may include three-dimensionally displaying a plurality of partial ultrasound images corresponding respectively to the plurality of ROIs.

The three-dimensional displaying of the plurality of partial ultrasound images corresponding respectively to the plurality of ROIs may include displaying the plurality of partial ultrasound images corresponding respectively to the plurality of ROIs in a side view.

The three-dimensional displaying of the plurality of partial ultrasound images corresponding respectively to the plurality of ROIs may include: adjusting sizes of the plurality of partial ultrasound images to a predetermined size; and displaying the plurality of size-adjusted partial ultrasound images overlappingly on the ultrasound image.

The three-dimensional displaying of the plurality of partial ultrasound images corresponding respectively to the plurality of ROIs may include three-dimensionally displaying a difference image between the plurality of partial ultrasound images corresponding respectively to the plurality of ROIs.

The selecting of the at least one ROI may include selecting an ROI having at least one of an elliptical shape, a tetragonal shape, and a free curve shape.

The three-dimensional displaying of the partial ultrasound image corresponding to the at least one ROI may include displaying the partial ultrasound image in at least one form of a gray scale map, a color scale map, a contour line map, a contour surface map, and a numerical value map.

According to one or more exemplary embodiments, an ultrasound apparatus includes: a display configured to display an ultrasound image of an object; a user input unit configured to receive a selection of at least one ROI in the ultrasound image; and a controller configured to convert image pixel information corresponding to the at least one ROI into height values and control the display to three-dimensionally display a partial ultrasound image corresponding to the at least one ROI by using the height values.

The controller may select an ROI of a predetermined size based on a point selected by a user.

The controller may select a region, which has a predetermined similarity value or more with respect to pattern information of a point selected by a user, in the ultrasound image as the ROI.

The controller may determine a sign of the height values based on movement direction information of a tissue or a bloodstream when the ultrasound image is a color Doppler image or a spectral Doppler image.

The display may display the three-dimensional (3D) partial ultrasound image overlappingly on the two-dimensional (2D) ultrasound image.

The controller may apply a semitransparent effect or a transparent effect to other images in the ultrasound image except a region in which the 3D partial ultrasound image is overlappingly displayed.

The display may three-dimensionally display the partial ultrasound image in a region different from a region in which the ultrasound image is displayed.

The controller may adjust at least one of a position, a rotation angle, and a size of the three-dimensionally displayed partial ultrasound image.

The display may further display at least one of an average height value, a maximum height value, a minimum height value, and a variance value of the partial ultrasound image.

The display may three-dimensionally display the partial ultrasound image by using a light source-based rendering method.

The user input unit may receive a selection of at least one rendering method among a plurality of rendering methods, and the display may three-dimensionally display the partial ultrasound image by the selected rendering method.

The at least one ROI may include a plurality of ROIs, and the display may three-dimensionally display a plurality of partial ultrasound images corresponding respectively to the plurality of ROIs.

The display may display the plurality of partial ultrasound images in a side view.

The controller may adjust sizes of the plurality of partial ultrasound images to a predetermined size and control the display to display the plurality of size-adjusted partial ultrasound images overlappingly on the ultrasound image.

The display may three-dimensionally display a difference image between the plurality of partial ultrasound images corresponding respectively to the plurality of ROIs.

BRIEF DESCRIPTION OF THE DRAWINGS

These and/or other aspects will become apparent and more readily appreciated from the following description of the exemplary embodiments, taken in conjunction with the accompanying drawings in which:

FIG. 3 is a flowchart of an ultrasound image display method according to an exemplary embodiment;

DETAILED DESCRIPTION

Figure 1:
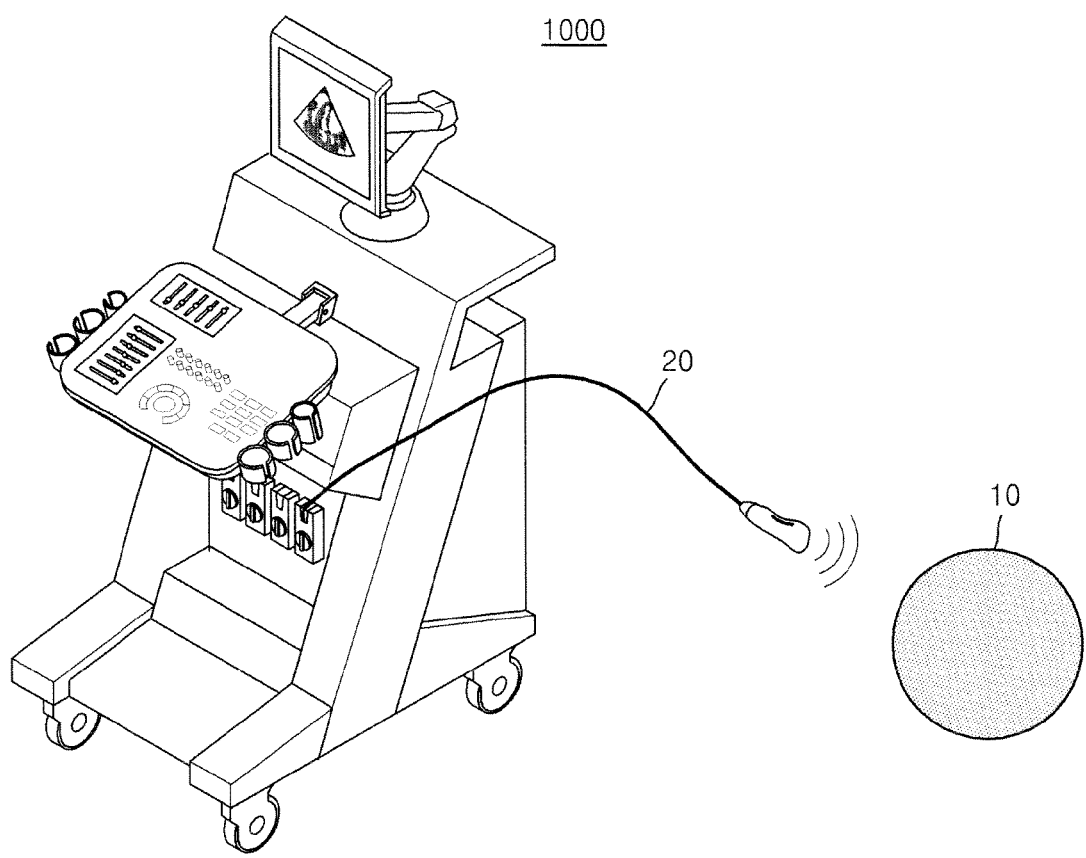
FIG. 1 is a perspective view of an ultrasound apparatus according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description. As used herein, expressions such as "at least one of," when preceding a list of elements, modify the entire list of elements and do not modify the individual elements of the list.

The terms used in this specification are those general terms currently widely used in the art in consideration of functions in regard to the present invention, but the terms may vary according to the intention of those of ordinary skill in the art, precedents, or new technology in the art. Also, specified terms may be selected by the applicant, and in this case, the detailed meaning thereof will be described in the detailed description of the inventive concept. Thus, the terms used in the specification should be understood not as simple names but based on the meaning of the terms and the overall description of the inventive concept.

When something "comprises" or "includes" a component, another component may be further included unless specified otherwise. Also, terms such as " . . . unit", " . . . module", or the like refer to units that perform at least one function or operation, and the units may be implemented as hardware or software or as a combination of hardware and software.

Throughout the specification, an "ultrasound image" refers to an image of an object obtained by using an ultrasound signal. The object may refer to a part of a body. For example, the object may include organs such as liver, heart, nuchal translucency (NT), brain, breast, and abdomen, or embryo.

Throughout the specification, a "user" may be, but is not limited to, a medical expert including a doctor, a nurse, a medical laboratory technologist, or a sonographer.

Reference will now be made in detail to exemplary embodiments, examples of which are illustrated in the accompanying drawings. The inventive concept may, however, be embodied in many different forms and should not be construed as being limited to the exemplary embodiments set forth herein. In addition, portions irrelevant to the description of the exemplary embodiments will be omitted in the drawings for a clear description of the exemplary embodiments, and like reference numerals will denote like elements throughout the specification.

FIG. 1 is a perspective view of an ultrasound apparatus 1000 according to an exemplary embodiment.

As illustrated in FIG. 1, the ultrasound apparatus 1000 may transmit an ultrasound signal to an object 10 through a probe 20. Then, the ultrasound apparatus 1000 may receive an ultrasound echo signal reflected from the object 10 and generate an ultrasound image.

In this specification, the ultrasound image may be implemented variously. For example, the ultrasound image may include, but is not limited to, at least one of a brightness (B) mode image representing a magnitude of an ultrasound echo signal reflected from the object 10 by brightness, a color Doppler image representing a speed of a moving object by color by using the Doppler effect, a spectral Doppler image representing an image of a moving object in the form of a spectrum by using the Doppler effect, a motion (M) mode image representing a time-dependent motion of an object at a predetermined position, and an elasticity mode image representing a difference between a reaction of an object when compression is applied to the object and a reaction of the object when compression is not applied to the object by an image.

According to an exemplary embodiment, the ultrasound image may be a two-dimensional (2D) image, a three-dimensional (3D) image, or a four-dimensional (4D) image. The ultrasound image will be descried below in detail with reference to FIGS. 2A, 2B, and 2C.

Figure 2A:
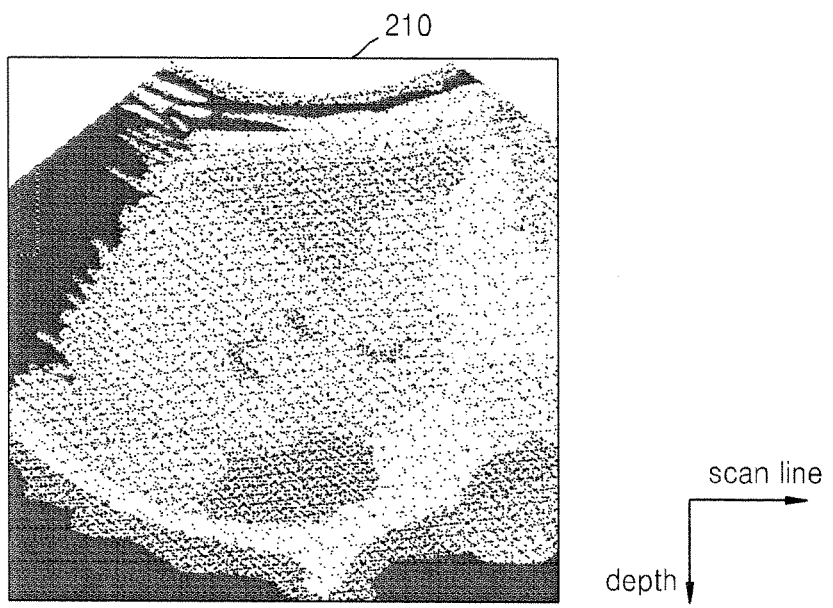
FIGS. 2A, 2B, and 2C are diagrams illustrating examples of an ultrasound image acquired by the ultrasound apparatus.
Figure 2B:
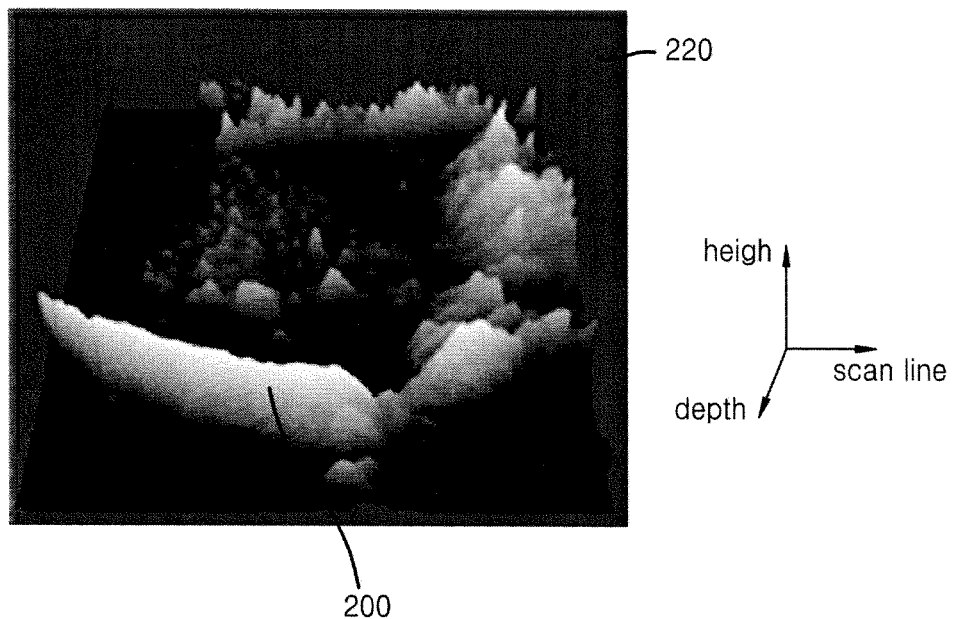
Figure 2C:
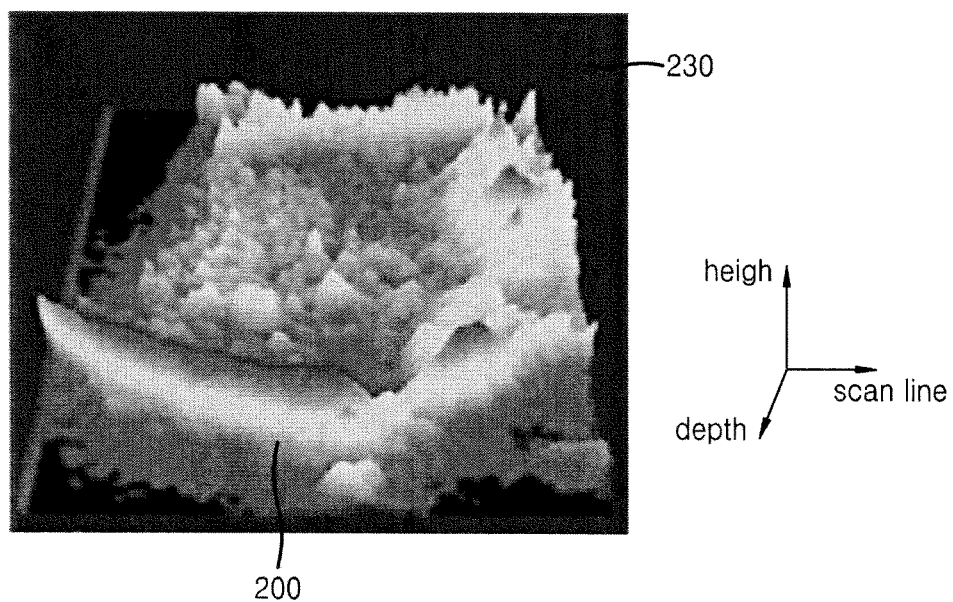

FIGS. 2A, 2B, and 2C are diagrams illustrating examples of an ultrasound image acquired by the ultrasound apparatus 1000.

As illustrated in FIG. 2A, according to an exemplary embodiment, the ultrasound apparatus 1000 may convert ultrasound image data into a brightness value and display an ultrasound image of the object 10 as a 2D B mode image 210. However, in some cases, the user may have difficulty in clearly detecting a brightness difference in the B mode image 210. Also, even when the ultrasound apparatus 1000 converts ultrasound image data into a color value and displays a 2D color mode image, the user may have difficulty in accurately detecting colors due to a individual difference such as a color sensitivity difference, an optical illusion, a color weakness, or a color blindness.

Thus, as illustrated in FIG. 2B, according to an exemplary embodiment, the ultrasound apparatus 1000 may convert image pixel information (e.g., a brightness value) acquired from ultrasound image data into height values. For example, the ultrasound apparatus 1000 may convert the 2D B mode image 210 into a height map 220 by using height values. In this specification, the height map 220 may refer to a 3D image that is displayed along a depth axis, a scan line axis, and a height axis.

According to an exemplary embodiment, the ultrasound apparatus 1000 may provide an ultrasound image as the height map 220, so that the user may intuitively detect a brightness difference in the ultrasound image by using a height difference.

As illustrated in FIG. 2C, according to an exemplary embodiment, the ultrasound apparatus 1000 may convert image pixel information (e.g., a brightness value) acquired from ultrasound image data into height values and color values and provide a color height map 230.

However, as illustrated in FIGS. 2B and 2C, when the entire ultrasound image is provided as the height map 220 or the color height map 230, since height values are very high in a region such as a diaphragm 200 having high brightness values, another image (e.g., liver parenchyma) around the diaphragm 200 may be covered. Thus, the ultrasound apparatus 1000 may need to provide only a portion of the ultrasound image as a height map.

Hereinafter, a method of displaying a portion of an ultrasound image as a 3D image having height values to enable the user to reduce an analysis error in the ultrasound image will be described in detail with reference to FIG. 3.

FIG. 3 is a flowchart of an ultrasound image display method according to an exemplary embodiment.

Referring to FIG. 3, in operation S310, the ultrasound apparatus 1000 may display an ultrasound image of an object.

According to an exemplary embodiment, the ultrasound apparatus 1000 may directly generate an ultrasound image of the object or may receive an ultrasound image of the object from an outside thereof. For example, the ultrasound apparatus 1000 may transmit an ultrasound signal to the object and generate an ultrasound image by using an ultrasound response signal reflected from the object. Also, the ultrasound apparatus 1000 may receive an ultrasound image from an external server or an external device.

The ultrasound image may include, but is not limited to, at least one of a brightness (B) mode image, a color Doppler image, a spectral Doppler image, a tissue Doppler image, an elasticity image, and a motion (M) mode image.

In operation S320, the ultrasound apparatus 1000 may select at least one region of interest (ROI) in the ultrasound image based on a user input. For example, the ultrasound apparatus 1000 may receive a user input for selecting an ROI in the ultrasound image.

According to an exemplary embodiment, various user inputs may be used to select the ROI. For example, the user input may include, but is not limited to, at least one of a key input, a touch input (e.g., a tap, a double tap, a touch & drag, a flick, or a swipe), a voice input, a motion input, and a multiple input.

According to an exemplary embodiment, the ROI may have various shapes. For example, the ROI may have, but is not limited to, a circular shape, an elliptical shape, a tetragonal shape, or a free curve shape. Also, the ROI may have various colors and various patterns.

According to an exemplary embodiment, the ultrasound apparatus 1000 may semi-automatically select the ROI. For example, the ultrasound apparatus 1000 may receive a selection of a specific point from the user. The ultrasound apparatus 1000 may select an ROI of a predetermined size (e.g., 10 pixels or 5 cm$^2$) based on a point selected by the user. The predetermined size may be preset by the user or by the ultrasound apparatus 1000.

Also, the ultrasound apparatus 1000 may select a region, which has a predetermined similarity value or more with respect to pattern information of a point selected by the user, in the ultrasound image as the ROI. For example, the ultrasound apparatus 1000 may select a region, which has a similar pattern value to a point selected by the user, as the ROI by using the following equations (Equations 1 to 3) that are used to analyze texture characteristics such as a gray level co-occurrence matrix (GLCM), entropy, and mutual information.

A GLCM method calculates the relationship between a brightness value of a current pixel and a brightness value of an adjacent pixel as a basic statistic such as an average, a contrast, or a correlation, allocates the calculation value as a new brightness value to a center pixel in a tunnel, and represents a partial texture characteristic of an input image. Those of ordinary skill in the art will readily understand the following equations, and thus detailed descriptions thereof will be omitted.

$$Co(i, j) = \frac{1}{N} \text{ cardinality} \quad \text{The } co-\text{occurrence matrix}(Co) \quad \text{Equation 1}$$
$$\{((k, l), (m, n)) \in ROI : |k - m| = dx, |l - n| = dy,$$
$$\text{sign}((k - l) \cdot (l - n)) = \text{sign}(dx \cdot dy), g(k, l) = i, g(m, n) = j\}$$

$$ENT = -\sum\nolimits_{i,j \in G} Co(i, j) \cdot \log(Co(i, j)) : \text{Uncertainty} \quad \text{Equation 2}$$

$$COR = \frac{\sum_{i,j \in G} ijCo(i, j) - m_x \cdot m_y}{S_x \cdot S_y} : \text{Similarity} \quad \text{Equation 3}$$

$m_x \cdot m_y$ : Average frequency of brightness $i, j$
$S_x \cdot S_y$ : Standard deviation According to an exemplary embodiment, the ultrasound apparatus 1000 may receive a selection of at least one ROI through a graphical user interface (GUI). This will be described later in detail with reference to FIG. 4A.

In operation S330, the ultrasound apparatus 1000 may convert image pixel information corresponding to at least one ROI into height values. According to an exemplary embodiment, the image pixel information, which represent values of pixels displayed on a screen, may include, but is not limited to, at least one of a brightness value, a speed value, a color value, an elasticity value, an amplitude value of a sound reflection signal, and a sound impedance value.

According to an exemplary embodiment, the ultrasound apparatus 1000 may convert brightness values included in the ROI into height values by using a first mapping table representing a correlation between brightness values and height values. In this case, the height values may increase as the brightness values increases; however, embodiments are not limited thereto.

Also, the ultrasound apparatus 1000 may convert color values included in the ROI into height values by using a second mapping table representing a correlation between a color value and a height value. Also, the ultrasound apparatus 1000 may convert speed values or elasticity values included in the ROI into height values.

According to an exemplary embodiment, the ultrasound apparatus 1000 may determine a sign of the height values based on movement direction information of a tissue or a bloodstream when the ultrasound image is a color Doppler image or a spectral Doppler image. For example, when the movement direction or a tissue or a bloodstream is a first direction, the ultrasound apparatus 1000 may determine the height values as a positive value; and when the movement direction or a tissue or a bloodstream is a second direction, the ultrasound apparatus 1000 may determine the height values as a negative value.

The ultrasound apparatus 1000 may also determine a sign (e.g., a plus sign or a minus sign) of the height values with respect to other directional image data in addition to Doppler image data (e.g., color Doppler image data or spectral Doppler image data).

In operation S340, the ultrasound apparatus 1000 may three-dimensionally display a partial ultrasound image corresponding to at least one ROI by using the height values.

According to an exemplary embodiment, the ultrasound apparatus 1000 may three-dimensionally display a partial ultrasound image in an ROI of the ultrasound image. For example, the ultrasound apparatus 1000 may display a 3D partial ultrasound image overlappingly on the ultrasound image. In this case, the ultrasound apparatus 1000 may three-dimensionally display a partial ultrasound image corresponding to at least one ROI in the ultrasound image and may two-dimensionally display the other images.

According to another exemplary embodiment, the ultrasound apparatus 1000 may three-dimensionally display a partial ultrasound image in a second region different from a first region in which the ultrasound image is displayed.

According to an exemplary embodiment, the ultrasound apparatus 1000 may provide additional information related to the partial ultrasound image. For example, the ultrasound apparatus 1000 may display at least one of an average height value, a maximum height value, a minimum height value, and a variance value of the partial ultrasound image.

According to an exemplary embodiment, the ultrasound apparatus 1000 may display the 3D partial ultrasound image as a gray scale map or a color scale map. For example, the ultrasound apparatus 1000 may display the 3D partial ultrasound image such that a higher portion is brighter and a lower portion is darker. Also, the ultrasound apparatus 1000 may display the 3D partial ultrasound image such that a higher portion is redder and a lower portion is bluer.

According to an exemplary embodiment, the ultrasound apparatus 1000 may display the 3D partial ultrasound image in at least one form of a contour line map, a contour surface map, and a numerical value map. For example, the ultrasound apparatus 1000 may display a contour line, a contour surface, or a numerical value in the 3D partial ultrasound image.

According to an exemplary embodiment, the ultrasound apparatus 1000 may transparently or semi-transparently display the other images except an ultrasound image corresponding to at least one ROI among the entire ultrasound image displayed based on the ultrasound image data.

According to an exemplary embodiment, the ultrasound apparatus 1000 may three-dimensionally display a partial ultrasound image corresponding to at least one ROI by using a light source-based rendering method. The light source-based rendering method (e.g., ray tracing) refers to a rendering method that traces a virtual visible ray to determine a color of a pixel. For example, the light source-based rendering method may process an object surface brightness, a light reflection effect, and a light refraction effect in the relationship between light and an object.

According to an exemplary embodiment, the ultrasound apparatus 1000 may receive a selection of at least one rendering method among a plurality of rendering methods and three-dimensionally display the partial ultrasound image corresponding to at least one ROI by the selected rendering method. The rendering method described herein may include, but is not limited to, a shading-based rendering method, a light source-based rendering (e.g., ray tracing) method, a radiosity-based rendering method, a volume rendering method, an image-based rendering (IBR) method, and a non-photorealistic rendering (NPR) method. Hereinafter, for convenience of description, the shading-based rendering method and the light source-based rendering method (e.g., ray tracing) will be described as examples. The shading-based rendering method calculates the brightness of an object based on the properties of light.

According to an exemplary embodiment, when the user selects a plurality of ROIs, the ultrasound apparatus 1000 may three-dimensionally display partial ultrasound images corresponding respectively to the plurality of ROIs. For example, the ultrasound apparatus 1000 may display a first partial ultrasound image corresponding to a first ROI and a second partial ultrasound image corresponding to a second ROI as a height map.

In this case, according to an exemplary embodiment, the ultrasound apparatus 1000 may display the 3D first partial ultrasound image and the 3D second partial ultrasound image overlappingly on the ultrasound image, or may display the 3D first partial ultrasound image and the 3D second partial ultrasound image separately from the ultrasound image.

According to an exemplary embodiment, when the first ROI and the second ROI have different sizes, the first partial ultrasound image and the second partial ultrasound image may have different sizes. In this case, the ultrasound apparatus 1000 may adjust the size of at least one of the first partial ultrasound image and the second partial ultrasound image before displaying the first partial ultrasound image and the second partial ultrasound image overlapping on the ultrasound image.

According to an exemplary embodiment, the ultrasound apparatus 1000 may adjust the size of the first partial ultrasound image and the size of the second partial ultrasound image to a predetermined size and display the size-adjusted first and second partial ultrasound images overlappingly on the ultrasound image. For example, the ultrasound apparatus 1000 may adjust the size of the first partial ultrasound image and the size of the second partial ultrasound image to the same size (e.g., 3×4 pixels) and display the same-size first and second partial ultrasound images overlappingly on the ultrasound image. Also, the ultrasound apparatus 1000 may adjust the size of the first partial ultrasound image to the size of the second partial ultrasound image and display the resulting first and second partial ultrasound images overlappingly on the ultrasound image.

Figure 4A:
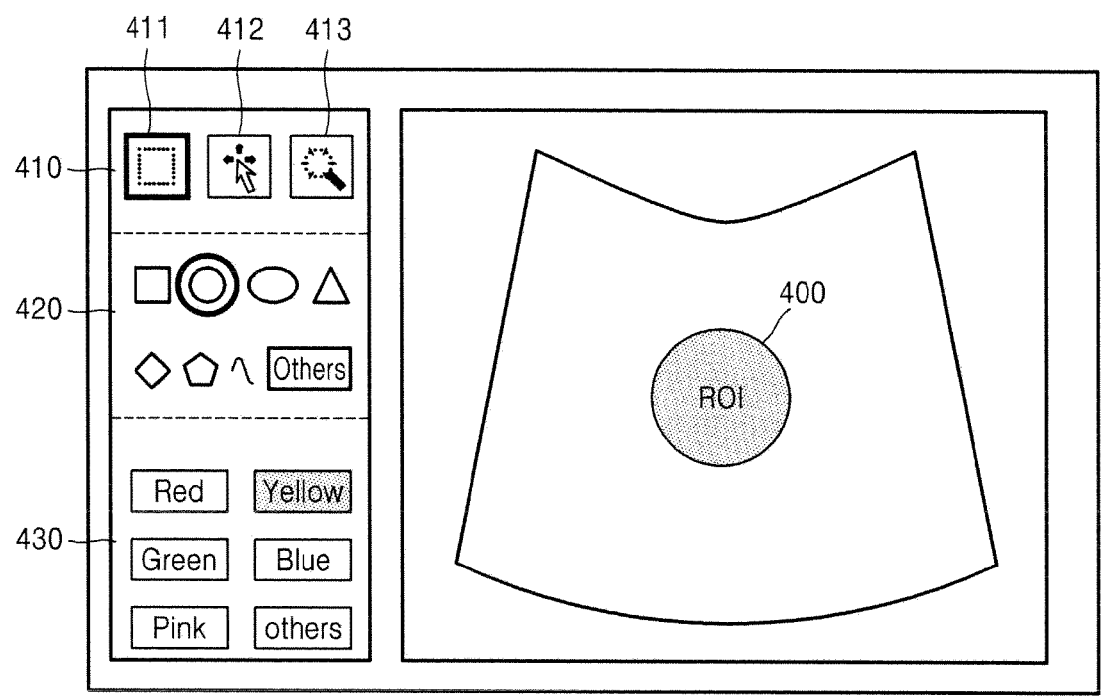
FIGS. 4A and 4B are diagrams illustrating a graphical user interface (GUI) for selecting a region of interest (ROI) according to an exemplary embodiment.
Figure 4B:
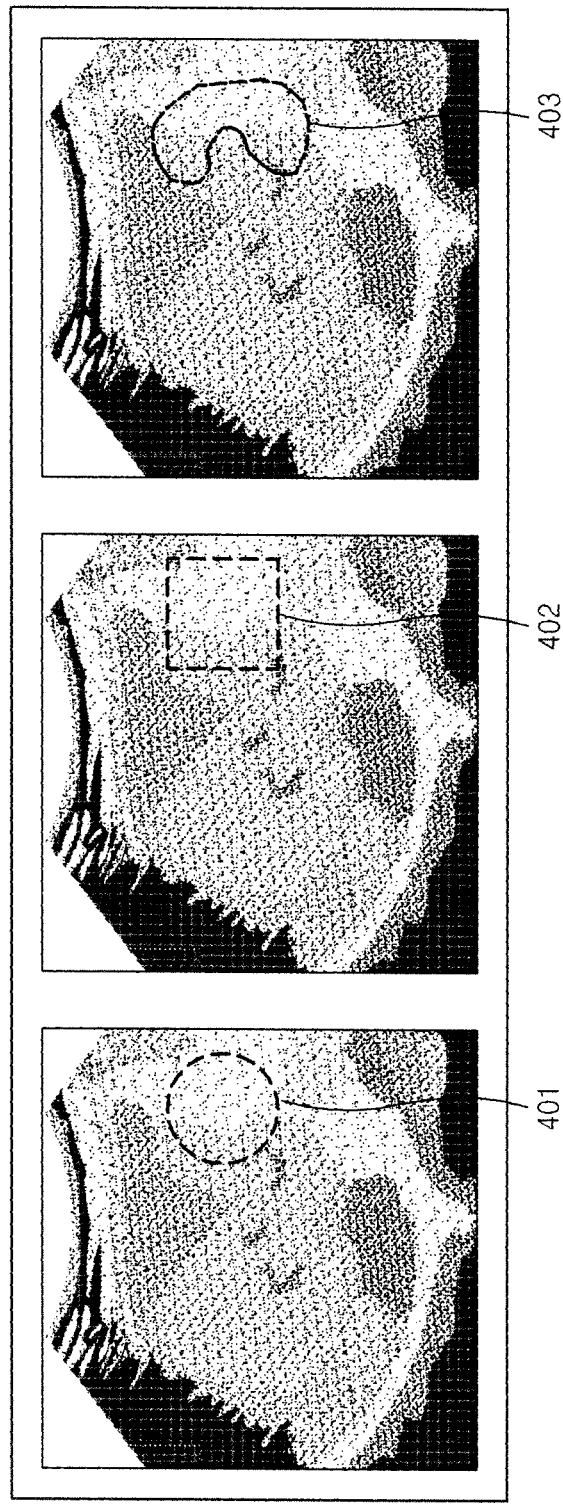

FIGS. 4A and 4B are diagrams illustrating a GUI for selecting an ROI according to an exemplary embodiment.

As illustrated in FIG. 4A, the ultrasound apparatus 1000 may provide a tool list 410 for selecting an ROI 400. For example, the ultrasound apparatus 1000 may provide a template button 411, a pointer button 412, and a magic button 413.

When the user selects the template button 411, the ultrasound apparatus 1000 may provide a template list 420. A template may be a figure used to select the ROI 400. The template list 420 may include, but is not limited to, a circle, a cone, an ellipse, a tetragon, a pentagon, a triangle, and a free curve. For example, as illustrated in FIG. 4B, the user may select a circular ROI 401, a tetragonal ROI 402, or a free-curve ROI 403.

According to an exemplary embodiment, when the user selects a circle from the template list 420, the ultrasound apparatus 1000 may display a circle on an ultrasound image. In this case, the user may select the ROI 400 by changing the position or size of the circle displayed on the ultrasound image.

According to another exemplary embodiment, the user may select the ROI 400 by drawing a line on the ultrasound image by using a touch tool (e.g., a finger or an electronic pen), a mouse, or a track ball.

When the user selects the pointer button 412 and selects a first point in the ultrasound image, the ultrasound apparatus 1000 may select an ROI of a predetermined size (e.g., a circle having a radius of about 2 cm, an ellipse having an about 2 cm major axis and an about 1 cm minor axis, or a tetragon having an area of about 4 $cm^2$) based on the first point.

Also, when the user selects the magic button 413, the ultrasound apparatus 1000 may display a magic icon for selecting a desired point. When the user moves the magic icon and selects a second point in the ultrasound image, the ultrasound apparatus 1000 may select a region having a pattern, which is similar to a pattern of the second point, as the ROI 400. For example, the ultrasound apparatus 1000 may select a region having a color value, which is equal or similar to a color value of the second point, as the ROI 400. Also, when the user selects a desired point in a tumor, the ultrasound apparatus 1000 may automatically select a tumor portion having similar pattern information (e.g., similar brightness) to the desired point, as the ROI 400.

According to an exemplary embodiment, the ultrasound apparatus 1000 may also provide a color list 430 for enabling the user to add a color to the ROI 400. In this case, the user (e.g., a sonographer) may add a color to the ROI 400 to increase the discrimination of the ROI 400.

Figure 5A:
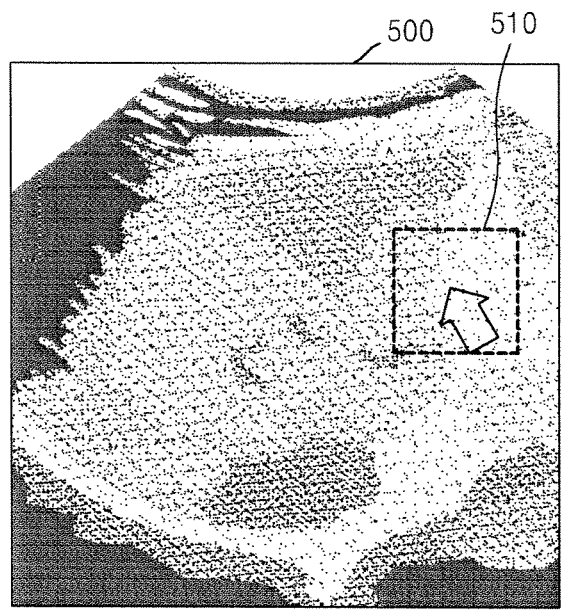
FIGS. 5A, 5B, and 5C are diagrams illustrating an example in which the ultrasound apparatus according to an exemplary embodiment three-dimensionally displays a partial ultrasound image in an ROI.
Figure 5B:
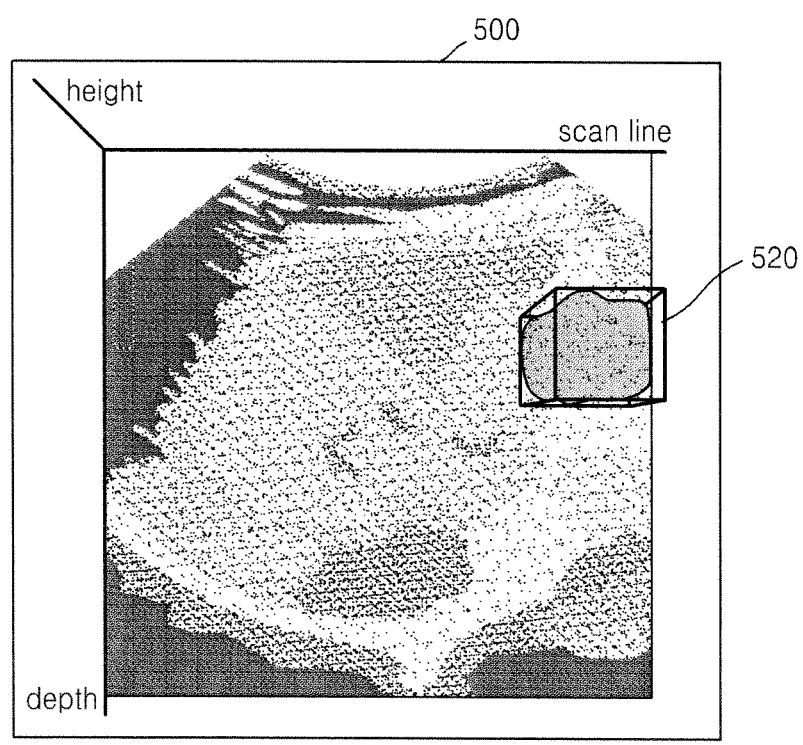
Figure 5C:
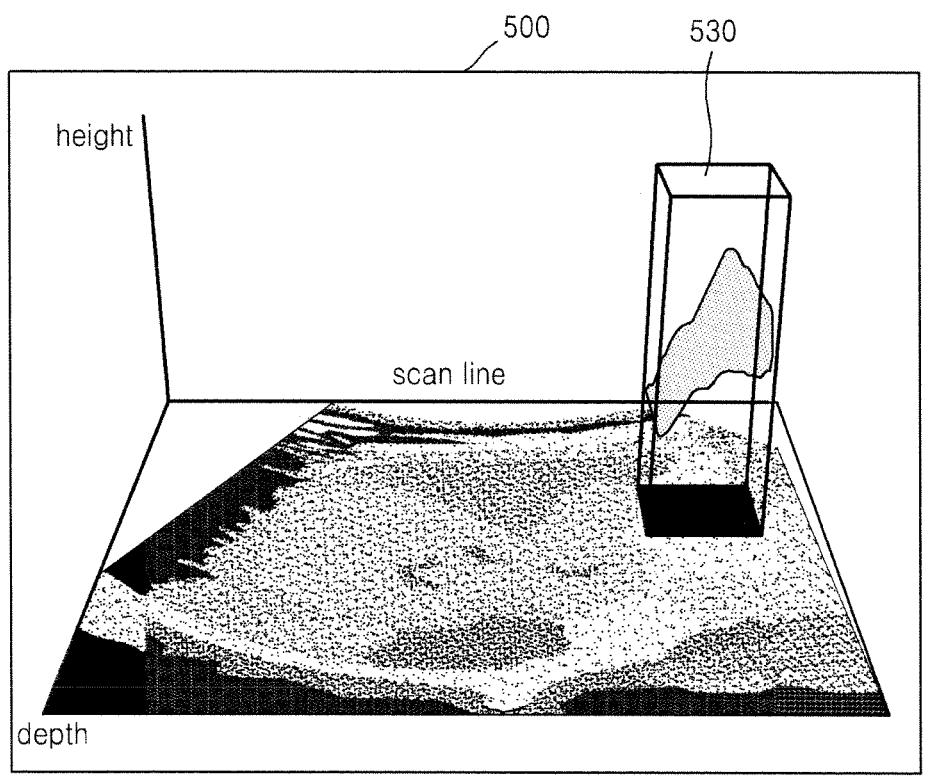

FIGS. 5A, 5B, and 5C are diagrams illustrating an example in which the ultrasound apparatus 1000 according to an exemplary embodiment three-dimensionally displays a partial ultrasound image in an ROI.

As illustrated in FIG. 5A, according to an exemplary embodiment, the ultrasound apparatus 1000 may receive a selection of a partial region in an ultrasound image 500 as an ROI 510. For example, when the user places a pointer at a desired point, the ultrasound apparatus 100 may select the ROI 510 of a predetermined size based on the desired point.

In this case, the ultrasound apparatus 1000 may convert brightness values included in the ROI 510 into height values. The ultrasound apparatus 1000 may generate a 3D partial ultrasound image 520 of the ROI 510 by using the height values.

As illustrated in FIG. 5B, the ultrasound apparatus 1000 may display the 3D partial ultrasound image 520 overlappingly on the ultrasound image 500. For example, the ultrasound apparatus 1000 may display the 3D partial ultrasound image 520 on the ROI 510. In this case, the user may clearly detect a brightness value in the ROI 510 based on the 3D partial ultrasound image 520.

As illustrated in FIG. 5C, the ultrasound apparatus 1000 may also display the 3D partial ultrasound image 530 in a side view. In this case, the user may observe height values in the ROI 510 in a front side view.

Figure 6:
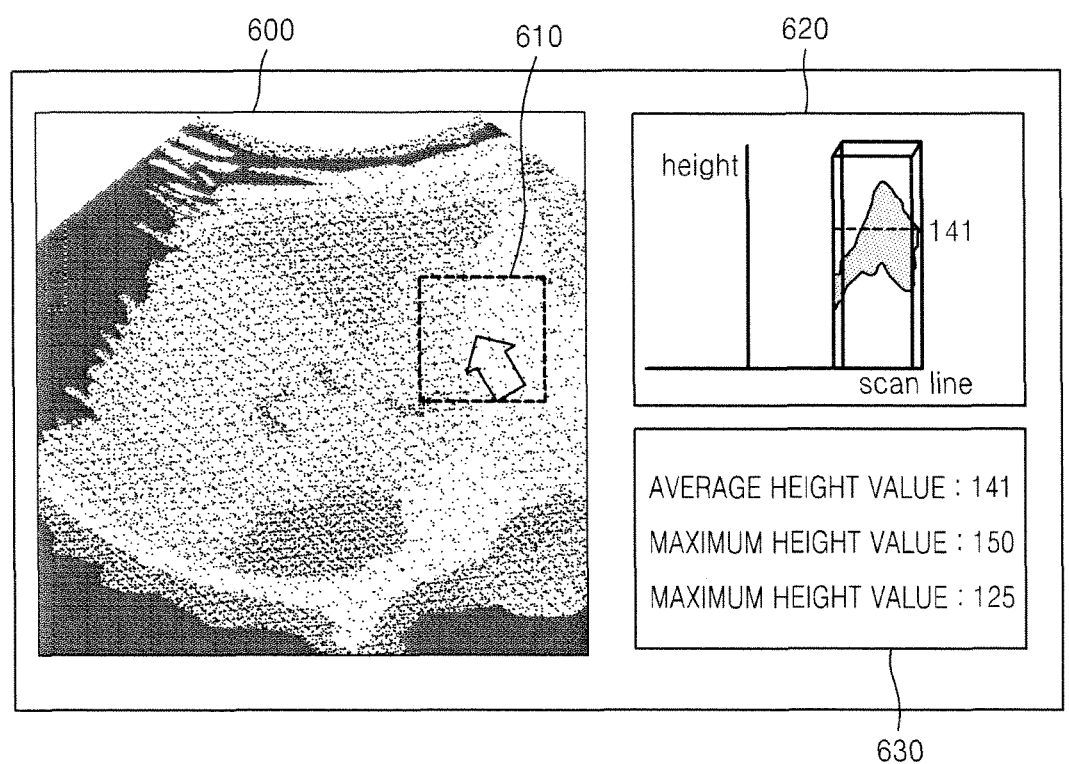
FIG. 6 is a diagram illustrating an example in which the ultrasound apparatus according to an exemplary embodiment displays a three-dimensional (3D) partial ultrasound image separately from an ultrasound image.

FIG. 6 is a diagram illustrating an example in which the ultrasound apparatus 1000 according to an exemplary embodiment displays a 3D partial ultrasound image separately from an ultrasound image.

As illustrated in FIG. 6A, according to an exemplary embodiment, the ultrasound apparatus 1000 may receive a selection of a center region (e.g., liver parenchyma) in an ultrasound image 600 as an ROI 610. In this case, the ultrasound apparatus 1000 may convert brightness values included in the ROI 610 into height values. The ultrasound apparatus 1000 may generate a 3D partial ultrasound image 620 of the ROI 610 by using the height values.

According to an exemplary embodiment, the ultrasound apparatus 1000 may display the 3D partial ultrasound image 620 in a separate region from the ultrasound image 600. Also, according to an exemplary embodiment, the ultrasound apparatus 1000 may display the 3D partial ultrasound image 620 with an increased or decreased size than the ROI 610.

Also, according to an exemplary embodiment, the ultrasound apparatus 1000 may display additional information 630 related to the 3D partial ultrasound image 620. For example, the ultrasound apparatus 1000 may display an average height value of 141, a maximum height value of 150, and a minimum height value of 125 as the additional information 630.

According to an exemplary embodiment, the ultrasound apparatus 1000 may move the position of the 3D partial ultrasound image 620, adjust the size of the 3D partial ultrasound image 620, or rotate the 3D partial ultrasound image 620 is a predetermined direction. Also, the ultrasound apparatus 1000 may display the 3D partial ultrasound image 620 as a gray scale map or a color scale map, and may display a contour line, a contour surface, and a numerical value in the 3D partial ultrasound image 620.

FIGS. 7A, 7B, 8A, and 8B are diagrams illustrating an example in which a partial ultrasound image corresponding to a specific color according to an exemplary embodiment is displayed three-dimensionally.

Figure 7A:
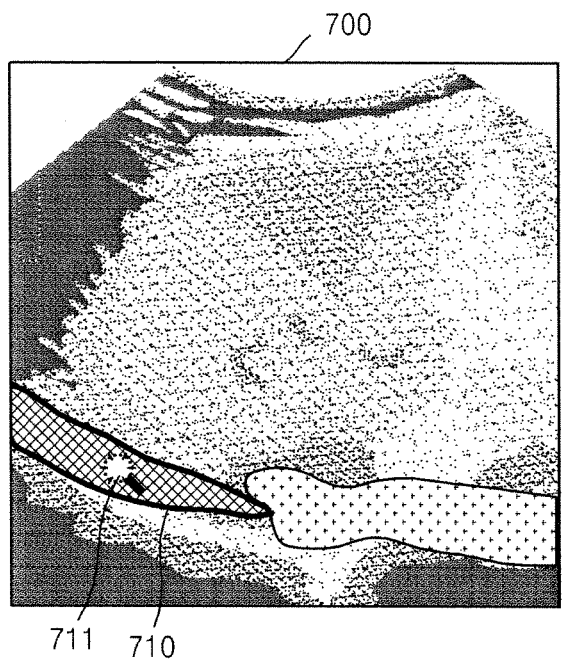
FIGS. 7A, 7B, 8A, and 8B are diagrams illustrating an example in which a partial ultrasound image corresponding to a specific color according to an exemplary embodiment is displayed three-dimensionally.

As illustrated in FIG. 7A, the ultrasound apparatus 1000 may display a color Doppler image 700. In this case, the ultrasound apparatus 1000 may represent a bloodstream moving toward the probe 20 in a red color and represent a bloodstream moving away from the probe 20 in a blue color.

According to an exemplary embodiment, the ultrasound apparatus 1000 may select a red region as an ROI 710 based on a user input. For example, when the user touches a red region with a magic icon 711, the ultrasound apparatus 1000 may select the red region as the ROI 710.

Figure 7B:
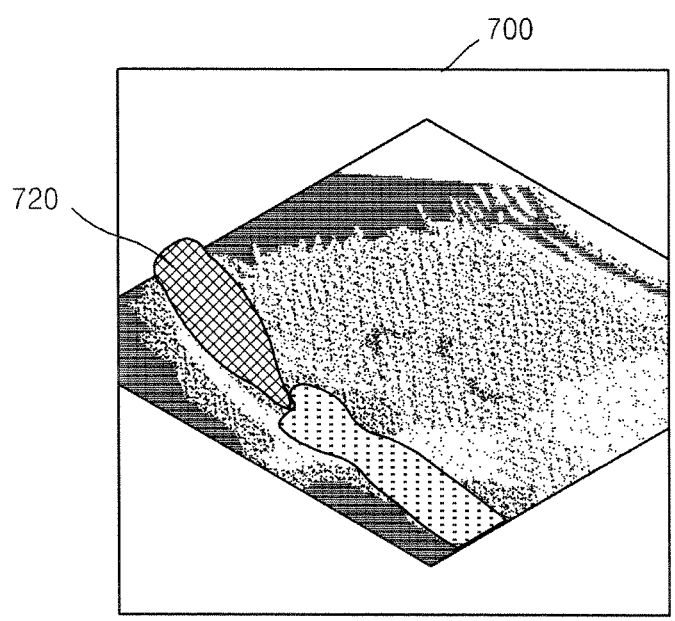

As illustrated in FIG. 7B, the ultrasound apparatus 1000 may convert color values of the ROI 710 into height values. For example, a red color may be converted into a positive (+) height value. The ultrasound apparatus 1000 may display a 3D partial ultrasound image 720 in the ROI 710 by using positive (+) height values. For example, the 3D partial ultrasound image 720 may be displayed as if it rises.

Figure 8A:
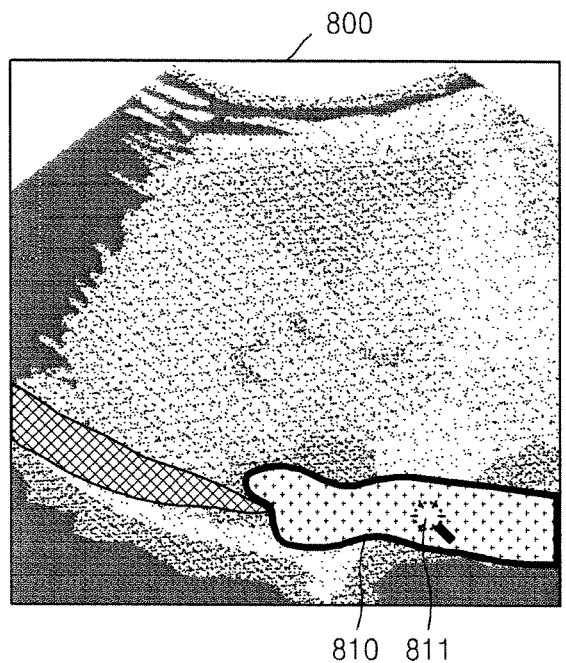

As illustrated in FIG. 8A, the ultrasound apparatus 1000 may select a blue region as an ROI 810 based on a user input. For example, when the user touches a blue region with a magic icon 811, the ultrasound apparatus 1000 may select the blue region as the ROI 810.

Figure 8B:
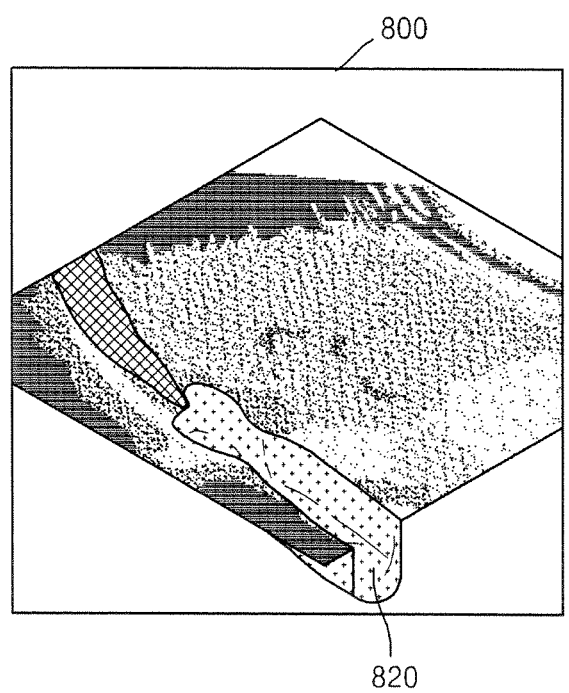

As illustrated in FIG. 8B, the ultrasound apparatus 1000 may convert color values of the ROI 810 into height values. For example, a blue color may be converted into a negative (−) height value. The ultrasound apparatus 1000 may display a 3D partial ultrasound image 820 in the ROI 810 by using negative (−) height values. For example, the 3D partial ultrasound image 820 may be displayed as if it is recessed.

While FIG. 7B/8B illustrates an example in which the 3D partial ultrasound image 720/820 is displayed in the ROI 710/810 of the ultrasound image 700/800, the 3D partial ultrasound image 720/820 may also be displayed separately from the ultrasound image 700/800.

Figure 9A:
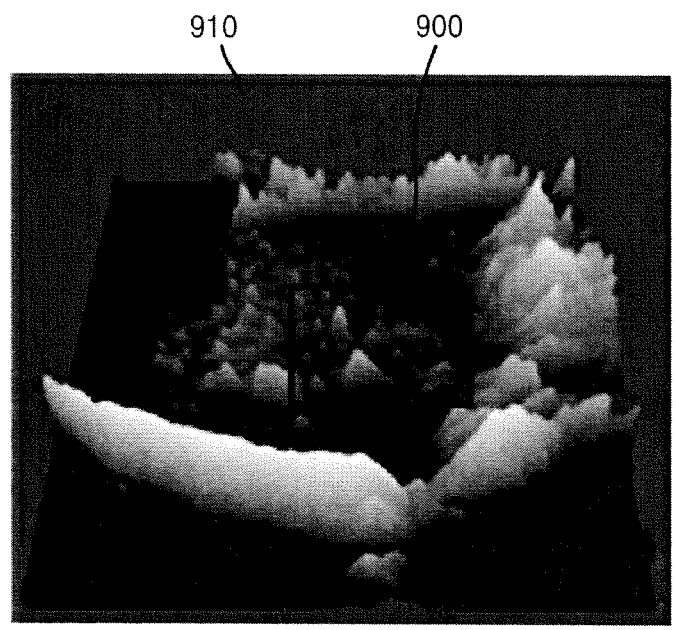
FIGS. 9A, 9B, and 9C are diagrams illustrating an example in which the ultrasound apparatus displays a partial ultrasound image corresponding to an ROI in a height map.
Figure 9B:
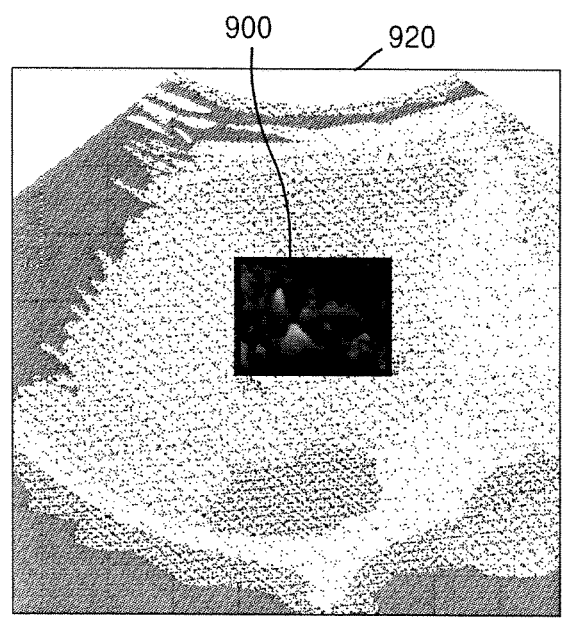
Figure 9C:
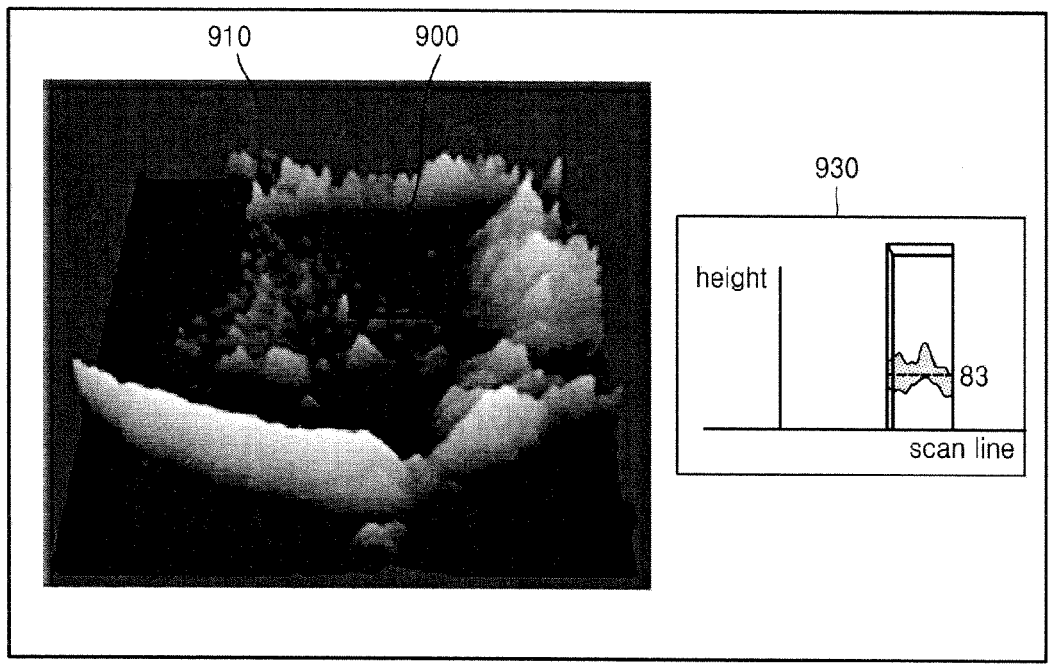

FIGS. 9A, 9B, and 9C are diagrams illustrating an example in which the ultrasound apparatus 1000 displays a partial ultrasound image corresponding to an ROI in a height map.

As illustrated in FIG. 9A, the ultrasound apparatus 1000 may convert image pixel information (e.g., a brightness value) acquired from ultrasound image data into height values. For example, the ultrasound apparatus 1000 may display a 3D height map 910 by using height values. In this case, while the user desires to detect a texture of a liver parenchyma, since a diaphragm having a high height value covers the liver parenchyma, the user may have difficulty in detecting the texture of the liver parenchyma.

According to an exemplary embodiment, the user may select the liver parenchyma as an ROI 900.

As illustrated in FIG. 9B, according to an exemplary embodiment, the ultrasound apparatus 1000 may convert and display the other regions except the ROI 900 as a 2D image 920. According to another exemplary embodiment, the ultrasound apparatus 1000 may apply a semitransparent effect or a transparent effect to the other images except a partial ultrasound image in the ROI 900.

Also, as illustrated in FIG. 9C, the ultrasound apparatus 1000 may display a 3D partial ultrasound image 930 corresponding to the ROI 900 in a separate region from the height map 910. In this case, the ultrasound apparatus 1000 may display the 3D partial ultrasound image 930 with an increased or decreased size. Also, the ultrasound apparatus 1000 may display a height value (e.g., an average height value of 83) in the 3D partial ultrasound image 930.

Figure 10:
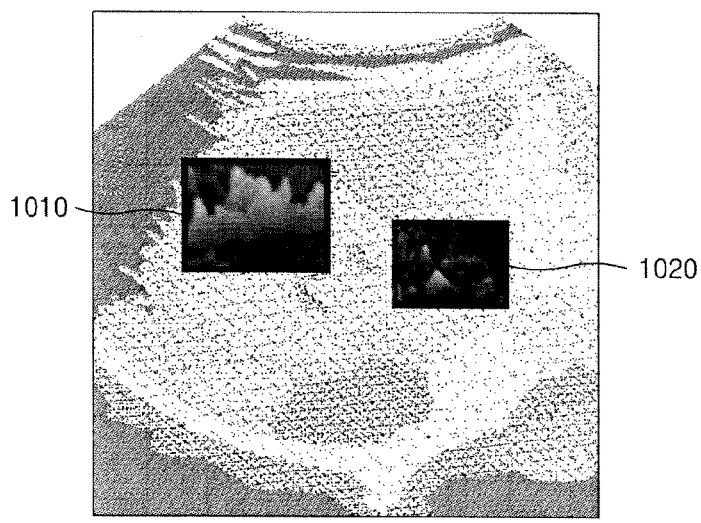
FIG. 10 is a diagram illustrating an example in which the ultrasound apparatus according to an exemplary embodiment three-dimensionally displays a plurality of partial ultrasound images corresponding respectively to a plurality of ROIs.

FIG. 10 is a diagram illustrating an example in which the ultrasound apparatus 1000 according to an exemplary embodiment three-dimensionally displays a plurality of partial ultrasound images corresponding respectively to a plurality of ROIs.

As illustrated in FIG. 10, based on a user input, the ultrasound apparatus 1000 may select a liver portion in an abdominal ultrasound image as a first ROI 1010 and select a kidney portion as a second ROI 1020. In this case, the ultrasound apparatus 1000 may convert brightness values in the first ROI 1010 and brightness values in the second ROI 1020 into height values. By using the height values, the ultrasound apparatus 1000 may generate a 3D first partial ultrasound image corresponding to the first ROI 1010 and a 3D second partial ultrasound image corresponding to the second ROI 1020. Since an average brightness value of the first ROI 1010 is greater than an average brightness value of the second ROI 1020, an average height value of the first partial ultrasound image may be greater than an average height value of the second partial ultrasound image.

According to an exemplary embodiment, the ultrasound apparatus 1000 may display the 3D first partial ultrasound image in the first ROI 1010 and display the 3D second partial ultrasound image in the second ROI 1020.

Figure 11:
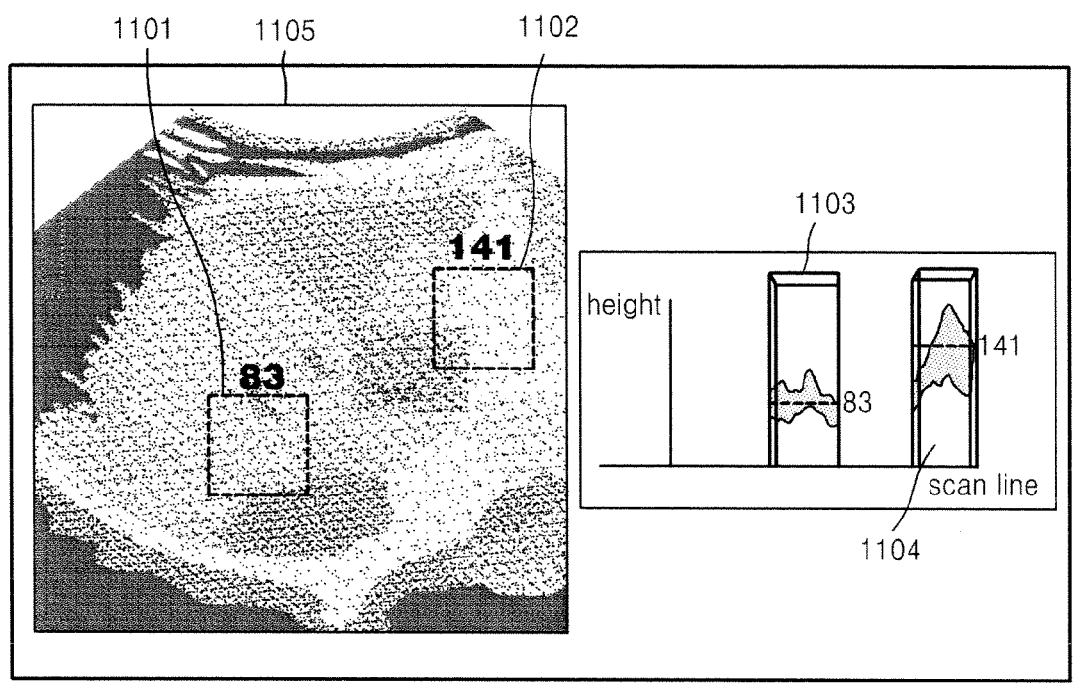
FIG. 11 is a diagram illustrating an example in which a plurality of 3D partial ultrasound images corresponding respectively to a plurality of ROIs are displayed separately from an ultrasound image.

FIG. 11 is a diagram illustrating an example in which a plurality of 3D partial ultrasound images corresponding respectively to a plurality of ROIs are displayed separately from an ultrasound image.

As illustrated in FIG. 11, the ultrasound apparatus 1000 may select a first ROI 1101 and a second ROI 1102 in an abdominal ultrasound image 1105 based on a user input. In this case, the ultrasound apparatus 1000 may convert brightness values in the first ROI 1101 and brightness values in the second ROI 1102 into height values. By using the height values, the ultrasound apparatus 1000 may generate a 3D first partial ultrasound image 1103 corresponding to the first ROI 1101 and a 3D second partial ultrasound image 1104 corresponding to the second ROI 1102. Since an average brightness value of the first ROI 1101 is smaller than an average brightness value of the second ROI 1102, an average height value (e.g., 83) of the first partial ultrasound image 1103 may be smaller than an average height value (e.g., 141) of the second partial ultrasound image 1104.

According to an exemplary embodiment, the ultrasound apparatus 1000 may display the 3D first partial ultrasound image 1103 and the 3D second partial ultrasound image 1104 separately from the abdominal ultrasound image 1105. In this case, the ultrasound apparatus 1000 may display the 3D first partial ultrasound image 1103 and the 3D second partial ultrasound image 1104 in a side view.

According to an exemplary embodiment, the ultrasound apparatus 1000 may adjust at least one of the position, the rotation angle, and the size of the 3D first partial ultrasound image 1103 and the 3D second partial ultrasound image 1104. Also, the ultrasound apparatus 1000 may display the 3D first partial ultrasound image 1103 and the 3D second partial ultrasound image 1104 overlappingly on the abdominal ultrasound image 1105. In this case, the ultrasound apparatus 1000 may adjust the 3D first partial ultrasound image 1103 and the 3D second partial ultrasound image 1104 to the same size and display the same-size 3D first an second partial ultrasound images 1103 and 1104 overlappingly on the abdominal ultrasound image 1105.

Also, the ultrasound apparatus 1000 may three-dimensionally display a difference image between the 3D first partial ultrasound image 1103 and the 3D second partial ultrasound image 1104.

FIGS. 12A, 12B, 12C, 12D, and 12E are diagrams illustrating an operation of selecting a rendering method by the ultrasound apparatus 1000 according to an exemplary embodiment.

Figure 12C:
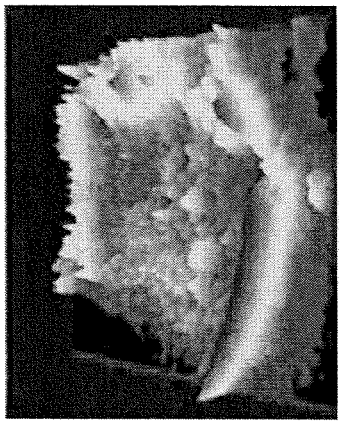
FIGS. 12A, 12B, 12C, 12D, and 12E are diagrams illustrating an operation of selecting a rendering method by the ultrasound apparatus according to an exemplary embodiment.
Figure 12E:
Figure 12B:
Figure 12D:
Figure 12A:
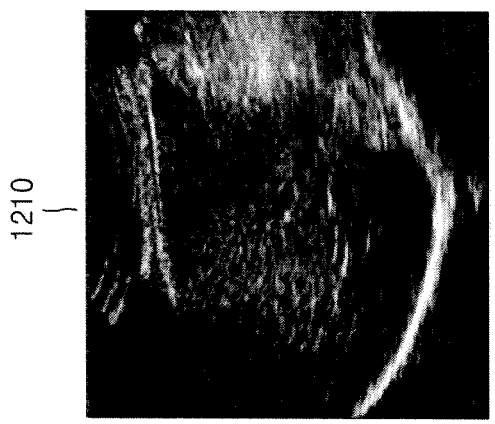

As illustrated in FIG. 12A, according to an exemplary embodiment, the ultrasound apparatus 1000 may acquire a 2D ultrasound image 1210 of a hepatic portal vein. In this case, the ultrasound apparatus 1000 may receive a selection of at least one rendering method among a plurality of rendering methods. The ultrasound apparatus 1000 may three-dimensionally display a partial ultrasound image corresponding to an ROI by the selected rendering method.

As illustrated in FIG. 12B, the ultrasound apparatus 1000 may receive a selection of a first rendering method that converts a brightness value into a height value based on a shading-based rendering method. In this case, the ultrasound apparatus 1000 may convert a brightness value corresponding to at least one ROI into a height value by the first rendering method. For example, the ultrasound apparatus 1000 may display a 3D gray image of the hepatic portal vein by converting a bright portion into high height values and converting a dark portion into low height values.

As illustrated in FIG. 12C, the ultrasound apparatus 1000 may receive a selection of a second rendering method that converts a brightness value into a height value and a color value based on a shading-based rendering method. In this case, the ultrasound apparatus 1000 may convert a brightness value corresponding to at least one ROI into a height value and a color value by the second rendering method. For example, the ultrasound apparatus 1000 may display a 3D color image of the hepatic portal vein by converting a bright portion into a red color having high height values and converting a dark portion into a blue color having low height values.

As illustrated in FIG. 12D, the ultrasound apparatus 1000 may receive a selection of a third rendering method that converts a brightness value into a height value based on a ray tracing-based rendering method. In this case, the ultrasound apparatus 1000 may display a 3D gray image of the hepatic portal vein by converting brightness values corresponding to at least one ROI into height values by the third rendering method and calculating brightness values and a transparency values at each sample point on a virtual ray.

As illustrated in FIG. 12E, the ultrasound apparatus 1000 may receive a selection of a fourth rendering method that converts a brightness value into a height value and a color value based on a ray tracing-based rendering method. In this case, the ultrasound apparatus 1000 may display a 3D color image of the hepatic portal vein by converting brightness values corresponding to at least one ROI into height values and color values by the fourth rendering method and calculating brightness values and transparency values at each sample point on a virtual ray.

Figure 13:
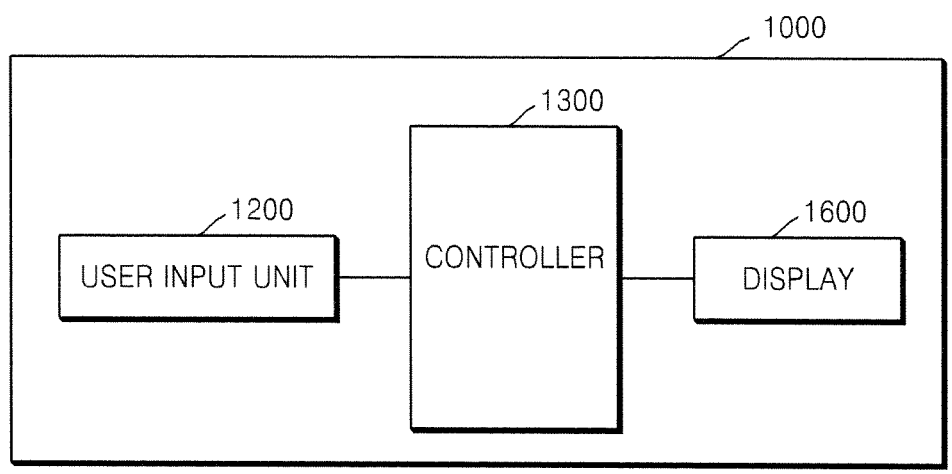
FIGS. 13 and 14 are block diagrams of an ultrasound apparatus according to an exemplary embodiment.
Figure 14:
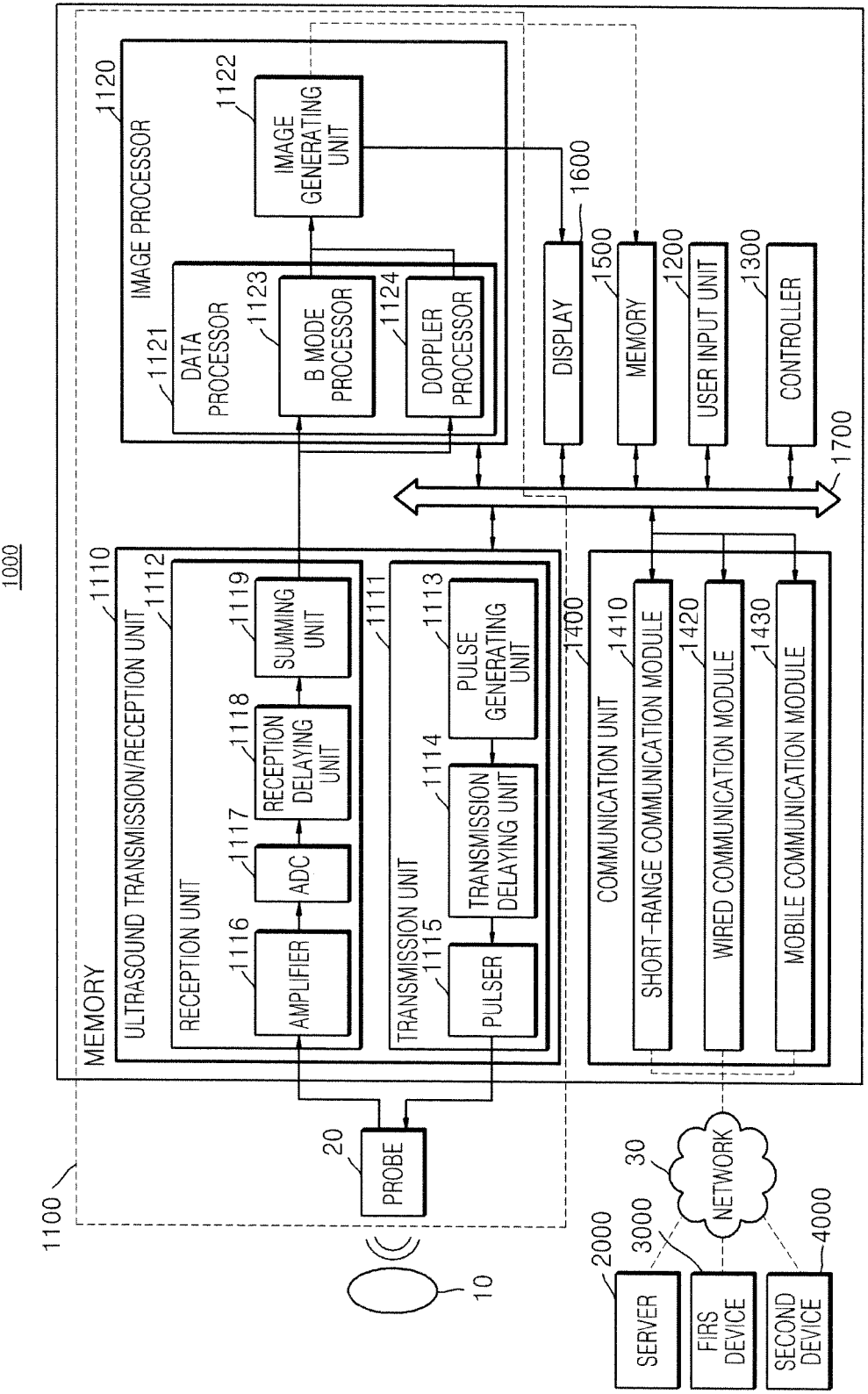

FIGS. 13 and 14 are block diagrams of an ultrasound apparatus 1000 according to an exemplary embodiment.

As illustrated in FIG. 13, the ultrasound apparatus 1000 according to an exemplary embodiment may include a user input unit 1200, a controller 1300, and a display 1600. However, all of the illustrated components are not necessary components. The ultrasound apparatus 1000 may include more or less components than the illustrated components. For example, as illustrated in FIG. 14, the ultrasound apparatus 1000 according to an exemplary embodiment may further include an ultrasound image acquiring unit 1100, a communication unit 1400, and a memory 1500 in addition to the user input unit 1200, the controller 1300, and the display 1600. The above components may be connected through a bus 1700.

The above components will be described below.

The ultrasound image acquiring unit 1100 according to an exemplary embodiment may acquire ultrasound image data of an object 10. The ultrasound image data according to an exemplary embodiment may be 2D ultrasound image data or 3D ultrasound image data of the object 10.

According to an exemplary embodiment, the ultrasound image acquiring unit 1100 may include a probe 20, an ultrasound transmission/reception unit 1110, and an image processing unit 1120.

The probe 20 transmits an ultrasound signal to the object 10 according to a driving signal applied from the ultrasound transmission/reception unit 1110 and receives an echo signal reflected from the object 10. The probe 20 includes a plurality of transducers, and the plurality of transducers oscillate according to an electrical signal transmitted thereto and generate an ultrasound wave, that is, acoustic energy. Also, the probe 20 may be connected to a main body of the ultrasound apparatus 1000 wiredly or wirelessly. According to embodiments, the ultrasound apparatus 1000 may include a plurality of probes 20. According to an exemplary embodiment, the probe 20 may include at least one of a one-dimensional (1D) probe, a 1.5D probe, a 2D (matrix) probe, and a 3D probe.

A transmission unit 1111 supplies a driving signal to the probe 20 and includes a pulse generating unit 1113, a transmission delaying unit 1114, and a pulser 1115. The pulse generating unit 1113 generates pulses for forming transmission ultrasound waves according to a predetermined pulse repetition frequency (PRF), and the transmission delaying unit 1114 applies a delay time for determining transmission directionality to the pulses. The pulses to which a delay time is applied correspond to a plurality of piezo-electric vibrators included in the probe 20, respectively. The pulser 1115 applies a driving signal (or a driving pulse) to the probe 20 at a timing corresponding to each pulse to which a delay time is applied.

A reception unit 1112 generates ultrasound data by processing echo signals received from the probe 20 and may include an amplifier 1116, an analog-digital converter (ADC) 1117, a reception delaying unit 1118, and a summing unit 1119. The amplifier 1116 amplifies echo signals in each channel, and the ADC 1117 analog-digital converts the amplified echo signals. The reception delaying unit 1118 applies delay times for determining reception directionality to the digital-converted echo signals, and the summing unit 1119 generates ultrasound image data by summing the echo signals processed by the reception delaying unit 1118.

The image processing unit 1120 generates an ultrasound image by scan-converting ultrasound image data generated by the ultrasound transmission/reception unit 1110. The ultrasound image may include not only a gray-scale ultrasound image obtained by scanning the object according to an amplitude (A) mode, a brightness (B) mode, and a motion (M) mode, but also a Doppler image representing a motion of a moving object by using a Doppler effect. The Doppler image may include a bloodstream Doppler image (also referred to as a color Doppler image) representing a flow of blood, a tissue Doppler image representing a motion of a tissue, and a spectral Doppler image representing a movement speed of an object in a waveform.

A B mode processing unit 1123 extracts B mode components from ultrasound image data and processes the B mode components. An image generating unit 1122 may generate an ultrasound image representing signal intensities as brightness based on the B mode components extracted by the B mode processing unit 1123.

Likewise, a Doppler processing unit 1124 may extract Doppler components from ultrasound image data, and the image generating unit 1122 may generate a Doppler image representing a motion of an object as colors or waveforms based on the extracted Doppler components.

The image generating unit 1122 according to an exemplary embodiment may generate a 3D ultrasound image through volume-rendering of volume data and may also generate an elasticity image that visualizes deformation of the object 10 due to a pressure.

In addition, the image generating unit 1122 may display various additional information in an ultrasound image by texts or graphics. For example, the image generating unit 1122 may add at least one annotation related to all or a portion of the ultrasound image to the ultrasound image. That is, the image generating unit 1122 may analyze the ultrasound image and add at least one annotation related to all or a portion of the ultrasound image to the ultrasound image based on the analysis result. Also, the image generating unit 1122 may add additional information corresponding to an ROI selected by the user to the ultrasound image.

The image processing unit 1120 may extract an ROI from the ultrasound image by using an image processing algorithm. In this case, the image processing unit 1120 may add a color, a pattern, or a frame to the ROI.

The image processing unit 1120 may convert image pixel information (e.g., a brightness value, a color value, a speed value, and an elasticity value) acquired from the ultrasound image data into height values. In this case, the image processing unit 1120 may convert image pixel information included in the ROI selected by the user into height values.

The user input unit 1200 refers to a unit through which the user (e.g., sonographer) inputs data for controlling the ultrasound apparatus 1000. For example, the user input unit 1200 may include, but is not limited to, a keypad, a dome switch, a touch pad (e.g., a capacitive overlay type, a resistive overlay type, an infrared beam type, a surface acoustic wave type, an integral strain gauge type, or a piezoelectric type), a track ball, and a jog switch. For example, the user input unit 1200 may further include various input units such as an electrocardiogram measuring module, a breath measuring module, a voice recognition sensor, a gesture recognition sensor, a fingerprint recognition sensor, an iris recognition sensor, a depth sensor, and a distance sensor.

According to an exemplary embodiment, the user input unit 1200 may detect not only a real touch but also a proximity touch. The user input unit 1200 may detect a touch input (e.g., a touch & hold, a tap, a double tap, or a flick) to the ultrasound image. Also, the user input unit 1200 may detect a drag input from a point at which a touch input is detected. The user input unit 1200 may detect a multi-touch input (e.g., a pinch) to at least two points included in the ultrasound image.

The user input unit 1200 may receive a selection of at least one ROI in the ultrasound image. In this case, various inputs may be used to select an ROI. Also, the ROI may have various shapes.

The user input unit 1200 may receive a selection of at least one rendering method among a plurality of rendering methods.

The controller 1300 may control overall operations of the ultrasound apparatus 1000. For example, the controller 1300 may control overall operations of the ultrasound image acquiring unit 1100, the user input unit 1200, the communication unit 1400, the memory 1500, and the display 1600.

The controller 1300 may convert image pixel information corresponding to at least one ROI into height values. The controller 1300 may determine a sign of the height values based on movement direction information of a tissue or a bloodstream when the ultrasound image is a color Doppler image or a spectral Doppler image.

The controller 1300 may control the display 1600 to three-dimensionally display a partial ultrasound image corresponding to at least one ROI by using the height values. The controller 1300 may apply a semitransparent effect or a transparent effect to the other images except the partial ultrasound image among the ultrasound image.

The controller 1300 may select an ROI of a predetermined size based on a point selected by the user. The controller 1300 may select a region, which has a predetermined similarity value or more with respect to pattern information of a point selected by the user, in the ultrasound image as the ROI.

The controller 1300 may adjust at least one of a position, a rotation angle, and a size of the 3D partial ultrasound image based on a user input.

The communication unit 1400 may include one or more components for enabling communication between the ultrasound apparatus 1000 and a server 2000, between the ultrasound apparatus 1000 and a first device 3000, and between the ultrasound apparatus 1000 and a second device 400. For example, the communication unit 1400 may include a short-range communication module 1410, a wired communication module 1420, and a mobile communication module 1430.

The short-range communication module 1410 refers to a module for short-range communication within a predetermined distance. Short-range communication technologies may include Wireless Local Area Network (LAN), Wi-Fi, Bluetooth, Bluetooth Low Energy (BLE), Ultra Wideband (UWB), Zigbee, Near Field Communication (NFC), Wi-Fi Direct (WFD), and Infrared Data Association (IrDA).

The wired communication module 1420 refers to a module for communication using electrical signals or optical signals. Examples of wired communication techniques according to an exemplary embodiment may include a pair cable, a coaxial cable, an optical fiber cable, and an Ethernet cable.

The mobile communication module 1430 communicates wireless signals with at least one of a base station, external devices (e.g., the first and second devices 3000 and 4000), and the server 2000 on a mobile communication network. Herein, the wireless signals may include voice call signals, video call signals, or various types of data for transmission and reception of text/multimedia messages.

The communication unit 100 is wiredly or wirelessly connected to a network 30 to communicate with an external device (e.g., the first device 3000 or the second device 4000) or the server 2000. The communication unit 1400 may exchange data with a hospital server or other medical apparatuses in a hospital connected through a Picture Archiving and Communication System (PACS). Also, the communication unit 1400 may perform data communication according to the Digital Imaging and Communications in Medicine (DICOM) standard.

The communication unit 1400 may transmit and receive data related to a diagnosis of the object 10, such as an ultrasound image, ultrasound image data, and Doppler image data of the object 10, through the network 30 and may also transmit and receive medical images captured by other medical devices, such as a CT image, a MRI image, and an X-ray image. In addition, the communication unit 1400 may receive information related to a diagnosis history or a treatment schedule of a patient from the server 2000 and utilize the information to diagnose the object 10.

The memory 1500 may store a program for processing of the controller 1300 and may store input/output data (e.g., ultrasound image data, a mapping table of a brightness value and a height value, a mapping table of a speed value and a height value, a mapping table of a color value and a height value, a mapping table of an elasticity value and a height value, information about an ROI, ultrasound images, testee information, probe information, body markers, and additional information).

The memory 1500 may include at least one type of storage medium from among flash memory type, hard disk type, multimedia card micro type, card type memory (e.g., SD and XD memories), random access memory (RAM), static random access memory (SRAM), read-only memory (ROM), electronically erasable programmable read-only memory (EEPROM), programmable read-only memory (PROM), magnetic memory, magnetic disk, and optical disk. Also, the ultrasound apparatus 1000 may utilize a web storage or a cloud server that functions as the memory 1500 on the Internet.

The display 1600 may display information processed in the ultrasound apparatus 1000. For example, the display 1600 may display an ultrasound image or may display a user interface (UI) or a graphical user interface (GUI) related to a control panel.

The display 1600 may display a partial region of the ultrasound image three-dimensionally and display the other regions two-dimensionally. For example, the display 1600 may display a partial ultrasound image corresponding to an ROI as a height map.

The display 1600 may three-dimensionally display a partial ultrasound image in the ROI of the ultrasound image. The display 1600 may three-dimensionally display a partial ultrasound image in a region different from a region in which the ultrasound image is displayed.

The display 1600 may three-dimensionally display a partial ultrasound image by using a light source-base rendering method. The display 1600 may three-dimensionally display a partial ultrasound image by a rendering method that is selected among a plurality of rendering methods by the user.

The display 1600 may display a 3D partial ultrasound image in at least one form of a gray scale map, a color scale map, a contour line map, a contour surface map, and a numerical value map.

The display 1600 may further display at least one of an average height value, a maximum height value, and a minimum height value of the partial ultrasound image. The display 1600 may three-dimensionally display a first partial ultrasound image corresponding to a first ROI and a second partial ultrasound image corresponding to a second ROI. In this case, the display 1600 may display the first partial ultrasound image and the second partial ultrasound image in a side view.

The display 1600 may display the 3D first partial ultrasound image and the 3D second partial ultrasound image overlappingly on the ultrasound image. In this case, the display 1600 may display the 3D first partial ultrasound image and the 3D second partial ultrasound image, which are adjusted to the same size by the controller 1300, overlappingly on the ultrasound image. The display 1600 may three-dimensionally display a difference image between the first partial ultrasound image and the second partial ultrasound image.

When the display 1600 includes a touchscreen with a layer structure of a touch pad, the display 1600 may be used as an input device in addition to an output device. The display 1600 may include at least one of a liquid crystal display, a thin film transistor liquid crystal display, an organic light-emitting diode, a flexible display, a 3D display, and an electrophoretic display. Also, the ultrasound apparatus 1000 may include two or more displays 1600 according to embodiments.

The methods according to the exemplary embodiments may be embodied in the form of program commands executable through various computer means, which may be recorded on a computer-readable recording medium. The computer-readable recording medium may include program commands, data files, and data structures either alone or in combination. The program commands recorded on the computer-readable recording medium may be those that are especially designed and configured for the inventive concept, or may be those that are known and available to computer programmers skilled in the art. Examples of the computer-readable recording medium include magnetic recording media such as hard disks, floppy disks and magnetic tapes, optical recording media such as CD-ROMs and DVDs, magneto-optical recording media such as floptical disks, and hardware devices such as ROMs, RAMs and flash memories that are especially configured to store and execute program commands. Examples of the program commands include machine language codes that may be generated by a compiler, and high-level language codes that may be executed by a computer by using an interpreter.

As described above, according to the one or more of the above exemplary embodiments, the ultrasound apparatus 1000 provides a 3D height map about an ROI of the user, thereby improving the convenience of an ultrasound diagnosis of the user. Also, an operation speed may be increased as compared with the case of providing an overall height map, and a height image of an ROI may be prevented from being covered by a height component of a region of uninterest (ROU).

It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the scope of the inventive concept as defined by the following claims.

What is claimed is:

1. An ultrasound image display method comprising:
   displaying an ultrasound image of an object;
   selecting at least one region of interest (ROI) in the ultrasound image based on a user input;
   converting image pixel information corresponding to the at least one ROI into height values, wherein the converting of the image pixel information into the height values comprises determining a sign of the height values based on movement direction information of a tissue or a bloodstream when the ultrasound image is a color Doppler image or a spectral Doppler image; and
   three-dimensionally displaying a partial ultrasound image corresponding to the at least one ROI by using the height values,
   wherein the three-dimensional displaying of the partial ultrasound image corresponding to the at least one ROI comprises displaying the three-dimensional (3D) partial ultrasound image overlappingly on the ultrasound image which is a two-dimensional (2D) form, and
   wherein the displaying of the 3D partial ultrasound image overlappingly on the ultrasound image which is the 2D form comprises applying a semitransparent effect or a transparent effect to other images in the ultrasound image which is the 2D form except a region in which the 3D partial ultrasound image is overlappingly displayed.

2. The ultrasound image display method of claim 1, wherein the ultrasound image comprises at least one of a brightness (B) mode image, a color Doppler image, a spectral Doppler image, a tissue Doppler image, an elasticity image, and a motion (M) mode image.

3. The ultrasound image display method of claim 1, wherein the image pixel information comprises at least one of a brightness value, a speed value, a color value, an elasticity value, an amplitude value of a sound reflection signal, and a sound impedance value.

4. The ultrasound image display method of claim 1, wherein the selecting of the at least one ROI comprises selecting an ROI of a predetermined size based on a point selected by a user.

5. The ultrasound image display method of claim 1, wherein the selecting of the at least one ROI comprises selecting a region, which has a predetermined similarity value or more with respect to pattern information of a point selected by a user, in the ultrasound image as the ROI.

6. The ultrasound image display method of claim 1, wherein the three-dimensional displaying of the partial ultrasound image corresponding to the at least one ROI comprises two-dimensionally displaying other images in the ultrasound image except the partial ultrasound image corresponding to the at least one ROI.

7. The ultrasound image display method of claim 1, wherein the three-dimensional displaying of the partial ultrasound image corresponding to the at least one ROI comprises three-dimensionally displaying the partial ultrasound image in a region different from a region in which the ultrasound image is displayed.

8. The ultrasound image display method of claim 1, further comprising adjusting at least one of a position, a rotation angle, and a size of the three-dimensionally displayed partial ultrasound image.

9. The ultrasound image display method of claim 1, further comprising displaying at least one of an average height value, a maximum height value, a minimum height value, and a variance value of the partial ultrasound image.

10. The ultrasound image display method of claim 1, wherein the three-dimensional displaying of the partial ultrasound image corresponding to the at least one ROI comprises three-dimensionally displaying the partial ultrasound image by using a light source-based rendering method.

11. The ultrasound image display method of claim 1, wherein the three-dimensional displaying of the partial ultrasound image corresponding to the at least one ROI comprises:
    receiving a selection of at least one rendering method among a plurality of rendering methods; and
    three-dimensionally displaying the partial ultrasound image by the selected rendering method.

12. The ultrasound image display method of claim 1, wherein
    the at least one ROI comprises a plurality of ROIs, and
    the three-dimensional displaying of the partial ultrasound image corresponding to the at least one ROI comprises three-dimensionally displaying a plurality of partial ultrasound images corresponding respectively to the plurality of ROIs.

13. The ultrasound image display method of claim 12, wherein the three-dimensional displaying of the plurality of partial ultrasound images corresponding respectively to the plurality of ROIs comprises displaying the plurality of partial ultrasound images corresponding respectively to the plurality of ROIs in a side view.

14. The ultrasound image display method of claim 12, wherein the three-dimensional displaying of the plurality of partial ultrasound images corresponding respectively to the plurality of ROIs comprises:

adjusting sizes of the plurality of partial ultrasound images to a predetermined size; and displaying the plurality of size-adjusted partial ultrasound images overlappingly on the ultrasound image.

15. The ultrasound image display method of claim 12, wherein the three-dimensional displaying of the plurality of partial ultrasound images corresponding respectively to the plurality of ROIs comprises three-dimensionally displaying a difference image between the plurality of partial ultrasound images corresponding respectively to the plurality of ROIs.

16. The ultrasound image display method of claim 1, wherein the selecting of the at least one ROI comprises selecting an ROI having at least one of an elliptical shape, a tetragonal shape, and a free curve shape.

17. The ultrasound image display method of claim 1, wherein the three-dimensional displaying of the partial ultrasound image corresponding to the at least one ROI comprises displaying the partial ultrasound image in at least one form of a gray scale map, a color scale map, a contour line map, a contour surface map, and a numerical value map.

18. A non-transitory computer-readable recording medium that stores a program that, when executed by a computer, performs the ultrasound image display method of claim 1.

19. An ultrasound apparatus comprising:

a display configured to display an ultrasound image of an object, wherein the display displays a three-dimensional (3D) partial ultrasound image overlappingly on the ultrasound image which is a two-dimensional (2D) ultrasound image;

a user input unit configured to receive a selection of at least one region of interest (ROI) in the ultrasound image; and a controller configured to convert image pixel information corresponding to the at least one ROI into height values having a sign, determined by the controller, based on movement direction information of a tissue or a bloodstream when the ultrasound image is a color Doppler image or a spectral Doppler image, and control the display to three-dimensionally display a partial ultrasound image corresponding to the at least one ROI by using the height values, wherein the controller applies a semitransparent effect or a transparent effect to other images in the ultrasound image which is the 2D ultrasound image except a region in which the 3D partial ultrasound image is overlappingly displayed.

20. The ultrasound apparatus of claim 19, wherein the controller selects an ROI of a predetermined size based on a point selected by a user.

21. The ultrasound apparatus of claim 19, wherein the controller selects a region, which has a predetermined similarity value or more with respect to pattern information of a point selected by a user, in the ultrasound image as the ROI.

22. The ultrasound apparatus of claim 19, wherein the display three-dimensionally displays the partial ultrasound image in a region different from a region in which the ultrasound image is displayed.

23. The ultrasound apparatus of claim 19, wherein the controller adjusts at least one of a position, a rotation angle, and a size of the three-dimensionally displayed partial ultrasound image.

24. The ultrasound apparatus of claim 19, wherein the display further displays at least one of an average height value, a maximum height value, a minimum height value, and a variance value of the partial ultrasound image.

25. The ultrasound apparatus of claim 19, wherein the display three-dimensionally displays the partial ultrasound image by using a light source-based rendering method.

26. The ultrasound apparatus of claim 19, wherein the user input unit receives a selection of at least one rendering method among a plurality of rendering methods, and the display three-dimensionally displays the partial ultrasound image by the selected rendering method.

27. The ultrasound apparatus of claim 19, wherein the at least one ROI comprises a plurality of ROIs, and the display three-dimensionally displays a plurality of partial ultrasound images corresponding respectively to the plurality of ROIs.

28. The ultrasound apparatus of claim 27, wherein the display displays the plurality of partial ultrasound images in a side view.

29. The ultrasound apparatus of claim 27, wherein the controller adjusts sizes of the plurality of partial ultrasound images to a predetermined size and controls the display to display the plurality of size-adjusted partial ultrasound images overlappingly on the ultrasound image.

30. The ultrasound apparatus of claim 27, wherein the display three-dimensionally displays a difference image between the plurality of partial ultrasound images corresponding respectively to the plurality of ROIs.

* * * * *